United States Patent [19]

Mankins et al.

[11] Patent Number: 4,958,060
[45] Date of Patent: Sep. 18, 1990

[54] CLAD METAL ELECTRODE

[75] Inventors: William L. Mankins, Huntington, W. Va.; David O. Gothard, Cary, N.C.; Charles P. Hardy, Kitts Hill, Ohio

[73] Assignee: Inco Alloys International, Inc., Huntington, W. Va.

[21] Appl. No.: 378,768

[22] Filed: Jul. 12, 1989

Related U.S. Application Data

[62] Division of Ser. No. 172,772, Mar. 28, 1988, Pat. No. 4,933,141.

[51] Int. Cl.$^5$ .............................................. B23K 35/02
[52] U.S. Cl. .......................... 219/145.22; 219/137 WM
[58] Field of Search ................... 219/145.22, 137 WM, 219/145.1

[56] References Cited

U.S. PATENT DOCUMENTS 3,118,053  1/1964  Arikawa et al. .................... 219/146
3,748,434  7/1973  Girard ............................ 219/145.22

*Primary Examiner*—Clifford C. Shaw
*Attorney, Agent, or Firm*—Blake T. Biederman; Francis J. Mulligan, Jr.; Edward A. Steen

[57] ABSTRACT

A clad metal electrode having a core, a sleeve and a consolidated metal powder therebetween bonding the sleeve to the core. The clad metal electrode is particularly useful with an iron rod core and compressed nickel powder between the iron rod and the nickel sleeve. The resultant clad welding rod permits higher operating amperages during welding operations.

3 Claims, 1 Drawing Sheet

CLAD METAL ELECTRODE

This is a divisional of copending application Ser. No. 07/172,772 filed on Mar. 28, 1988, now U.S. Pat. No. 4,933,141.

TECHNICAL FIELD

The instant invention relates to clad metal electrodes in general and, more particularly, to a clad metal electrode having powder as an intermediate layer.

BACKGROUND ART

Clad metal tubing, that is, a tube comprised of a tubular core or wire material internally or externally circumscribed by a dissimilar sleeve material, has been commercially available for many years. Offering a large array of differing physical and chemical characteristics, a composite structure may be fabricated to suit particular needs. The strength of the core material matched with selected properties of the cladding affords the engineer custom designed options that are superior to single material designs.

Various methods have been developed to coat metal surfaces. However, limitations exist with each presently known method. To illustrate, weld overlaying is commonly used to coat internal surfaces of articles of manufacture but such cladding requires essentially flat or cylindrical surfaces having little detail. There are also size limitations for such internal linings that are related to access by welding equipment. Similar limitations apply to the related processes, flame and plasma spraying which, although useful for internal cladding, provide coatings that may not be dense enough or thick enough for many applications. Welding and spraying methods can not be readily used to apply coatings of reactive metals such as titanium.

Although generally used on flat plate, explosive bonding and braze bonding are other methods that may be used for internal cladding. However, these processes are of limited use since they require precise mating of part and cladding.

Hot isostatic pressing is generally considered useful for forming powdered metal articles and is also useful for external metal cladding. It is conceivable that this process could also be used for the internal cladding of metal articles; however, the equipment used with this process is extremely sophisticated and requires considerable capital investment.

Composite tubing can be prepared by simultaneous extrusion of a powdered metal and a solid shell. This method is applicable to many materials. Unfortunately, high production costs translate into high selling prices and as a consequence limit the usage of these materials.

Turning now more particularly to extruding methods, a major difficulty is caused by the need for an intermediate can. The can must be first fabricated, positioned in place, processed and ultimately removed; each step increasing the cost of the technique. Moreover, as the diameter of the ultimate product becomes smaller, i.e. welding electrode, the use of a can becomes less desirable.

Representative examples of the prior powder art include U.S. Pat. No. 2,390,452 which teaches a method for welding dissimilar materials and U.S. Pat. Nos. 3,652,235 and 3,753,704 (a continuation-in-part thereof) which disclose an isostatic method of fabricating a clad product. U.S. Pat. No. 4,016,008 utilizes an internal metal liner or can which is generally removed. U.S. Pat. No. 4,065,306 utilizes an expandable bladder.

The instant invention is directed toward the expeditious production of tubular or rod goods of relatively lower cost and compatible quality when compared to existing methods.

SUMMARY OF THE INVENTION

Accordingly, there is provided a method for making a billet for extrusion without the need for a can to contain the cladding powder. As a result, smaller quantities of powder are needed.

Essentially, the method utilizes wrought or cast material for both the core and the sleeve. A space between the core and the sleeve is filled with a small quantity of powder that is consolidated during extrusion. By eliminating cans and bladders, the thickness of the space is not dimensionally critical. This permits relative ease of assembly of the extrusion billet.

The utilization of the powder insert between the core and the sleeve allows for dissimilar materials to be bonded together to form a composite cladded tube and rod. Inasmuch as physical dimensions are less critical with the instant method, the disclosed technique is useful for an entire array of shaped products such as tubes, pipe, squares, rod, wire and welding electrodes.

The advantages of the instant invention are:

(A) Ease of assembly.
(B) No preparation and removal of a can.
(C) Produces material that can be produced economically on conventional hot and cold working mill equipment and rotary forges.
(D) Requires minimal machining to produce component parts.
(E) Good bonding affinity between the core and the sleeve.
(F) No large quantity of powder required for the sleeve material.
(G) Method is amenable to tube and welding rod and wire products.
(H) Method permits a thin cladding layer to be placed on the outside diameter, the inside diameter or both surfaces of a tube.
(I) Method permits many alloy considerations without the attendant production of costly powders.

PREFERRED MODE FOR CARRYING OUT THE INVENTION

Figure 1:
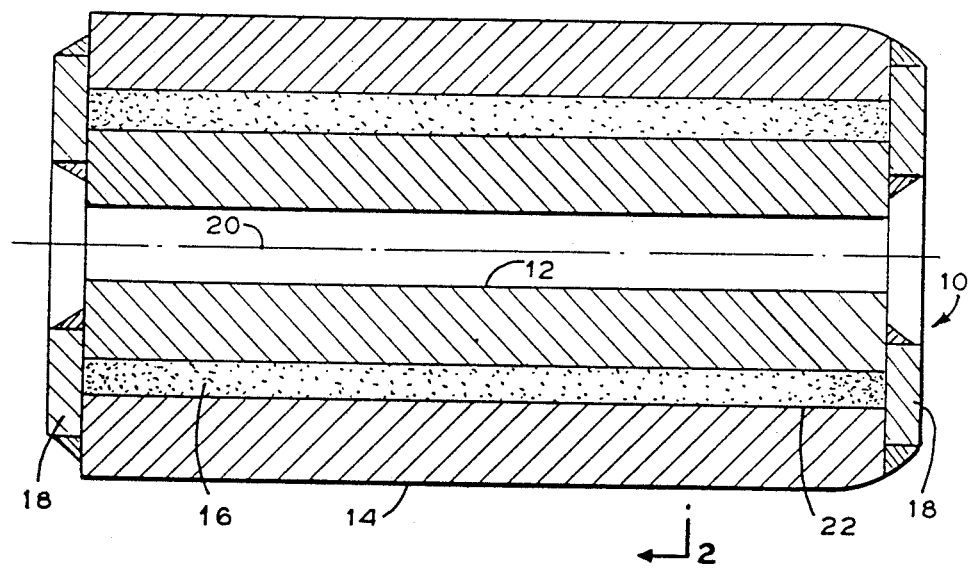
FIG. 1 is a cross sectional view of an embodiment of the invention.
Figure 2:
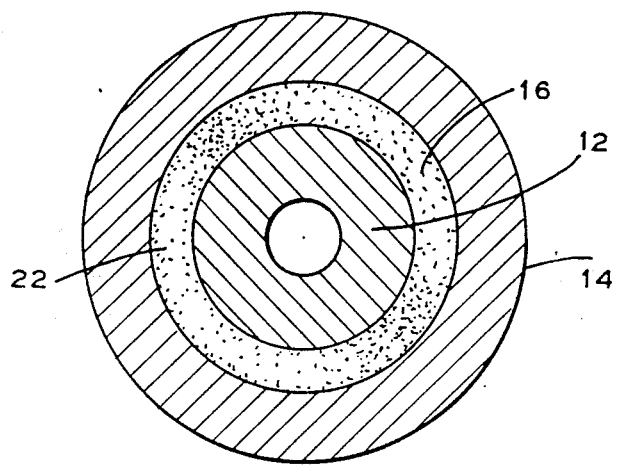
FIG. 2 is a view taken along line 2—2 in FIG. 1.

FIGS. 1 and 2 are cross sectional views of a billet 10 prior to extrusion. The billet 10 consists of a core 12, an external sleeve 14 and powder 16 disposed therebetween in the resultant annular space 22. End caps 18 seal in the powder 16. The axis of symmetry is represented by reference numeral 20.

The billet 10 may be prepared by vertically orienting the core 12 and sliding a spacer (not shown) having a thickness equal to the predetermined thickness of the space 22 over the core 12. The sleeve 14 is then slid over the spacer. One end cap 18 is welded to the top of the core 12 and the sleeve 14. All welds should be air tight. The billet 10 is then inverted, the spacer removed and the powder 16 is introduced to the space 22.

A small quantity of titanium sponge may be introduced into the space 22 before the powder 16 is fed into it. The titanium sponge serves as an oxygen getter during the subsequent sintering and billet heating process. This eliminates the need for evacuation of the billet 10 after powder filling. Eventually the titanium containing end portions of the extruded product may be cut off.

Depending on the materials selected the powder 16 may be a prealloyed, blended or single elemental powder.

To assist in filling the space 22, the billet 10 should be vibrated and a funnel used to feed the powder into the space 22.

After the space 22 has been filled with the powder 16 and additional titanium sponge, another end cap 18 is welded on the sleeve 14 and core 12 to complete the assembly of the billet 10. Rounding or radiusing the leading end of the billet 10 aids the extrusion process.

can be static or centrifugally cast or made from wrought or extruded products. The versatility of the method can be visualized with the following hypothetical example: Assume that a tube is being centrifugally cast as a sleeve for cladding on the outside diameter of some core material. The desired wall thickness of the tube centrifugally cast may be nominally one inch (2.54 cm) wall thickness but due to casting flaws or variability in the amount of metal cast, final wall thickness of the tube may be greater than or less than the desired thickness. The instant method provides latitude in accommodating the dimensional variations by using slightly more or less powder as required to achieve component wall thickness (in this case one inch [2.54 cm]).

Ten experimental extrusion billets were prepared as described above. Details are provided in the table below:

| Heat I.D. | Extrusion Temperature °F. | (°C.) | Die Size in. | (mm) | Throttle % | Billet Make-Up Outer Sleeve | Powder | Core |
|---|---|---|---|---|---|---|---|---|
| 2 | 2150 | (1177) | 0.750 | (19.1) | 34 | INCOLOY alloy 825 | INCOLOY alloy 825 | INCONEL alloy 625 |
| 3 | 2150 | (1177) | 0.750 | (19.1) | 34 | INCOLOY alloy 825 | INCONEL alloy 671 | INCONEL alloy 600 |
| 1 | 2150 | (1177) | 0.750 | (19.1) | 34 | INCOLOY alloy 825 | INCOLOY alloy 825 | INCONEL alloy 600 |
| 4 | 2150 | (1177) | 0.750 | (19.1) | 34 | INCOLOY alloy 825 | INCONEL alloy 671 | INCONEL alloy 625 |
| 5 | 2150 | (1177) | 0.750 | (19.1) | 34 | INCOLOY alloy 825 | NICKEL 123 | INCONEL alloy 600 |
| 6 | 2150 | (1177) | 0.750 | (19.1) | 34 | INCOLOY ALLOY 825 | NICKEL 123 | INCONEL ALLOY 625 |
| 7 | 2050 | (1121) | 0.750 | (19.1) | 34 | INCOLOY alloy 825 | INCOLOY alloy 825 | INCONEL alloy 600 |
| 8 | 2050 | (1121) | 0.750 | (19.1) | 34 | INCOLOY alloy 825 | INCOLOY alloy 825 | INCONEL alloy 625 |
| 9 | 2050 | (1121) | 0.750 | (19.1) | 34 | INCOLOY alloy 825 | NICKEL 123 | INCONEL alloy 600 |
| 10 | 2050 | (1121) | 0.750 | (19.1) | 34 | INCOLOY alloy 825 | NICKEL 123 | INCONEL alloy 625 |

Extrusion Comments:
4 - Melted. Suspect extrusion temperature too high for 625 core
6 - Same as #4
8 - Press malfunction
INCOLOY and INCONEL are trademarks of assignee In the instant invention, metal powders in small quantities are used to fill the air gap between the two major components of the clad products (irrespective of whether inside diameter or outside diameter clad material is being made). It has been demonstrated experimentally that the powder can be similar in or identical composition to either of the major components or dissimilar to both components.

Using previous techniques, clad tubing may be made by co-extrusion of two dissimilar metals that have been shrunk or press fitted together so that a metallurgical bond is achieved on extrusion or working. The use of interference fits to join the dissimilar metals requires costly very close tolerance machining, a means to heat or cool one of the components, and a pressing device for assembly. Contrary to current practice, powder is used in the instant invention to permit lower cost "sloppy" tolerance between the components to be joined and assembly can be accomplished without the use of presses. A role of the powder is that of a filler to compensate for differences in machined sizes of component parts.

Further cost reductions are achieved in the instant invention because the material used for the components The billets were extruded on Loewy ® hydropress (750-ton) {3,336 N}capacity) to an 0.750 inch (19.1 mm) diameter at an extrusion ratio of 21:1.

The combination of high extrusion temperatures, high extrusion ratios and the alloy combinations within the billets caused some initial problems. There was evidence of melting in some of the rods but good metallurgical bonds were obtained in all of the alloy combinations.

Photomicrographs of the extruded materials showed that sound metallurgical bonds were obtained with the three powders used. Thus, it can be concluded that the powder used to fill the annular space may be similar or identical in composition to one of the components or dissimilar to both materials. Accordingly, actual commercial practice will dictate the choice of components to obtain the desired mechanical and chemical properties of the finished product. Diffusion across boundary lines is minimal and not believed to pose any difficulties. Samples of the as-extruded rods were hot rolled from 0.750 inch (19.1 mm) diameter to 0.650 inch (16.5 mm) diameter as starting stock for cold rolling experiments.

They were annealed for 0.5 hour at 1850° F. (1010° C.) and cold rolled to 0.500 inch (12.7 mm) squares. The percent reduction was 24% cold work. The material rolled without incident. Photomicrographs showed that the bond integrity was maintained. Samples 4 and 6 that experienced melting were actually improved after cold rolling but some evidence of melting was still evident.

The above experiments had the width of the annular space as a variable. No effect was observed and it can be concluded that there could be a minimum, consistent with the ease of filling. If the powder used is of the same composition of one of the components comprising the core or sleeve, then its thickness can be apparently greatly expanded without detrimental effects on the final product.

Additional experiments were run to determine the applicability of the instant invention to clad or duplex welding electrodes. It is known that certain existing welding nickel-base electrodes are amperage limiting. Due to excess heating of the electrode, the welder must either turn down the amperage setting or waste the portion of the electrode that overheats. This inefficiency causes loss of both material and the welder's time.

By utilizing the instant method, it has been determined that a nickel-iron duplex electrode may be processed to wire and flux coated to produce electrodes that may be used at more than 20% higher amperage settings than current electrodes without overheating.

The resultant wire has either nickel or iron sheathing the other component. Nickel is the preferred sheathing material because it has a lower electrical resistivity thus allowing for higher electrical currents to be carried without overheating. In addition, nickel does not oxidize as does iron.

As with the production of tubing, the wire billet uses a metal powder between the components. This use of the powder permits the use of more liberal machining and rolling tolerances for preparation of the component parts. The powder aids in metallurgical bonding of tube component parts. An additional benefit over conventional methods of making duplex billets is that the costly requirement that the billet be extruded to a billet for hot rolling to wire rod has been eliminated. The duplex billet may be directly rotary forged to a rectangular section for hot rolling or hot rolled directly to wire rod. As a last step, conventional wire drawing processes may be utilized in reducing the wire to final size.

A series of comparison tests were conducted to determine the efficacy of the instant method with respect to welding electrodes.

METHOD 1

A nickel tube (3½ inch [89 mm] outside diameter, 2¼ inch [57 mm] inside diameter × 6½ inch [165 mm] long) was machined to have a 2.35+0.010 inch (60 mm) inside diameter. An iron (1010HR Steel) rod was machined to a 2.35−0.010 inch (60 mm) diameter and the two pieces were fit together and both ends welded at their mating surfaces. Both materials were acid pickled for oxide removal and solvent cleaned before assembly. Note that this method of billet assembly requires that both pieces require machining to close tolerance that adds to the cost of production.

METHOD 2

A nickel tube (3½ inch [89 mm] outside diameter, 3 inch [76 mm] inside diameter × 6½ inch [165 mm] long) was used as the outer sleeve. An iron rod was machined 2.35±0.020 inch (60 mm) diameter. Note that tolerances were much more liberal, which cuts machining costs. An end cap was welded to join the sleeve and core. The iron core was centered inside the nickel sleeve. The space was filled with Nickel 123 (essentially pure nickel) powder. Vibration was used to further pack the loose powder. The loose powder does not have the density of wrought nickel so that while the calculations show the nickel to be 58% of the weight, in actuality, the nickel weight approached 55%. After filling the space with powder, a cap was welded on the open end. The same cleaning procedures were used on this billet.

Both billets were charged into a furnace at 1950° F. (1066° C.) and heated four hours at temperature. Each billet was upset forged in an extrusion press at 500 tons (2224 N) against a blank die. After ejection from the press, both billets were reheated at 1950° F. (1066° C.) for about one hour and hot rolled to a 0.680 inch (17 mm) diameter rod. Material from Method 1 showed cracking of the nickel caused by breaking up of the core during rolling. The materials did not seem to roll as one and metallurgically bond but seemed to come apart as rolling progressed. The billet from Method 2 containing the nickel powder was rolled without incident to a high quality rod.

The 0.680 inch (17 mm) diameter hot rolled rod of Method 2 was annealed at 1850° F. (1010° C.)/0.5 hour, air cooled and cold rolled on an 8 inch (203 mm) rod mill to about 0.5 inch (18 mm), round cornered square, reannealed as above, cold rolled to 0.25 inch (6.3 mm) round, annealed as above, cold rolled on a 4 inch (102 mm) rod mill to 0.125 inch (3 mm) round cornered square. All cold work was done without incident.

The material was then cold drawn to 0.093 inch (2 mm) diameter using dry soap as a lubricant. A review of the cross sectional profiles of the wire as it was being processed indicated that the material became fully dense and would behave as a solid wire.

Comparing existing commercial electrodes with those made in accordance with this invention, calculations were undertaken to show the effects of electrode heating during welding. The material heating effect caused by the electrode carrying a current while welding is shown by the expression:

$$P_H = I^2 R \qquad [1]$$

where
$P_H$ = heat generated in watts
I = applied welding current in amperes
R = resistance of the material in ohms $$R = \frac{\rho L}{A} \qquad [2]$$

where
$\rho$ = resistivity in ohms × 10$^{-6}$ cm
L = electrode length in centimeters
A = cross section of electrode in square centimeters (0.04383 cm$^2$)
$\rho_{Ni}$ = 6.84 × 10$^{-6}$ ohm cm
$\rho_{Fe}$ = 9.7 × 10$^{-6}$ ohm cm
$\rho_{NiFe\ 258}$ = 30–35 × 10$^{-6}$ ohm cm
NiFe 258 is a conventional alloyed wire consisting of about 55% nickel and 45% iron.

The table below compares the heat generated by the various compositions:

| Material | Length, cm | R, Ohms | $P_H = I^2R$, Watts at 60 Amps | at 90 Amps |
|---|---|---|---|---|
| Ni | 30 | 0.00468 | 16.85 | 37.91 |
| Ni | 10 | 0.00156 | 5.62 | 12.64 |
| Fe | 30 | 0.00628 | 22.61 | 50.87 |
| Fe | 10 | 0.00209 | 7.52 | 16.93 |
| NiFe 258 | 30 | 0.02259 | 81.32 | 182.98 |
| NiFe 258 | 10 | 0.00753 | 27.11 | 60.99 |

It may be seen from the data in the preceding table that NiFe 258 produces about five times more heat than the nickel sheathed material and would produce about three and one-half times more heat than would an iron sheathed rod.

The nickel sheathed material would generate only about 75% as much heat as the iron sheathed electrode. The nickel sheathed electrode would also be protected from surface oxidation since iron oxidizes. Accordingly, it is preferable to put nickel on the outside surface.

Obviously, the nickel sheathed material could be used at higher amperage settings significantly higher than the NiFe 258 or higher settings than the iron. This is important to the welding industry.

0.093 inch (2.4 mm) diameter wire was made into 0.125 inch (3.2 mm) diameter coated electrodes for welding. They were compared to NI-ROD® welding electrode 55 and NI-ROD® welding electrode 55X. (NI-ROD is a trademark of assignee.)

These commercially available electrodes are made from NiFe 258 alloy. Tests indicated that the clad electrodes would operate at 110-120 amperes as compared to 90 amperes for the conventional electrodes.

While in accordance with the provisions of the statute, there is illustrated and described herein specific embodiments of the invention, those skilled in the art will understand that changes may be made in the form of the invention covered by the claims and that certain features of the invention may sometimes be used to advantage without a corresponding use of the other features.

The embodiments of the invention in which an exclusive property or privilege is claimed are defined as follows.

1. A clad welding electrode comprising a nickel tube, an iron rod within the nickel tube and consolidated nickel powder between the nickel tube and the iron rod bonding the nickel tube to the iron rod.

2. The welding electrode of claim 1 wherein the welding electrode is capable of operating at 110-120 amperes.

3. The welding electrode of claim 2 wherein the sleeve is coated.

* * * * *